(12) United States Patent
Zimmermann et al.

(10) Patent No.: US 9,759,684 B2
(45) Date of Patent: Sep. 12, 2017

(54) GAS ANALYZING DEVICE COMPRISING AN ION MOBILITY SPECTROMETER AND METHOD OF USING THE SAME

(71) Applicant: GOTTFRIED WILHELM LEIBNIZ UNIVERSITÄT HANNOVER, Hannover (DE)

(72) Inventors: Stefan Zimmermann, Burgwedel (DE); Philipp Cochems, Verden (DE); Jens Langejürgen, Hannover (DE); Ansgar Kirk, Hannover (DE)

(73) Assignee: Gottfried Wilhelm Leibniz Universitaet Hannover, Hannover (DE)

( * ) Notice: Subject to any disclaimer, the term of this patent is extended or adjusted under 35 U.S.C. 154(b) by 0 days.

(21) Appl. No.: 15/105,593

(22) PCT Filed: Dec. 10, 2014

(86) PCT No.: PCT/EP2014/077199
§ 371 (c)(1),
(2) Date: Jun. 20, 2016

(87) PCT Pub. No.: WO2015/091146
PCT Pub. Date: Jun. 25, 2015

(65) Prior Publication Data
US 2016/0305909 A1    Oct. 20, 2016

(30) Foreign Application Priority Data
Dec. 19, 2013   (DE) .................... 10 2013 114 421

(51) Int. Cl.
*G01N 27/62* (2006.01)
*H01J 49/40* (2006.01)
(Continued)

(52) U.S. Cl.
CPC .......... *G01N 27/622* (2013.01); *H01J 49/061* (2013.01)

(58) Field of Classification Search
CPC .... G01N 27/622; G01N 27/624; G01N 27/62; G01N 30/70; G01N 30/7206; G01N 33/22; G01N 23/2055; G01N 23/20058; H01J 49/0018; H01J 49/004; H01J 49/0031; H01J 49/066; H01J 49/0165; H01J 49/40; H01J 49/063; H01J 49/164; H01J 49/0013; H01J 49/0095; H01J 49/02; H01J 49/04;
(Continued)

(56) References Cited
U.S. PATENT DOCUMENTS 4,311,669 A * 1/1982 Spangler ................ G01N 27/62
                                                  422/83
4,378,499 A * 3/1983 Spangler .............. G01N 27/622
                                                  250/281
(Continued)

*Primary Examiner* — David A Vanore
(74) *Attorney, Agent, or Firm* — Whitham, Curtis & Cook, P.C.

(57) ABSTRACT

A gas analyzing device including at least one ion mobility spectrometer is provided. The gas analyzing device also includes an energy supply device interacting with a reaction chamber of the ion mobility spectrometer which is designed to manipulate the density of free reactant ions in the reaction chamber by supplying energy. A method for analyzing gas by means of a gas analyzing device according to the ion mobility spectrometry is also provided.

12 Claims, 8 Drawing Sheets

Figure 5:
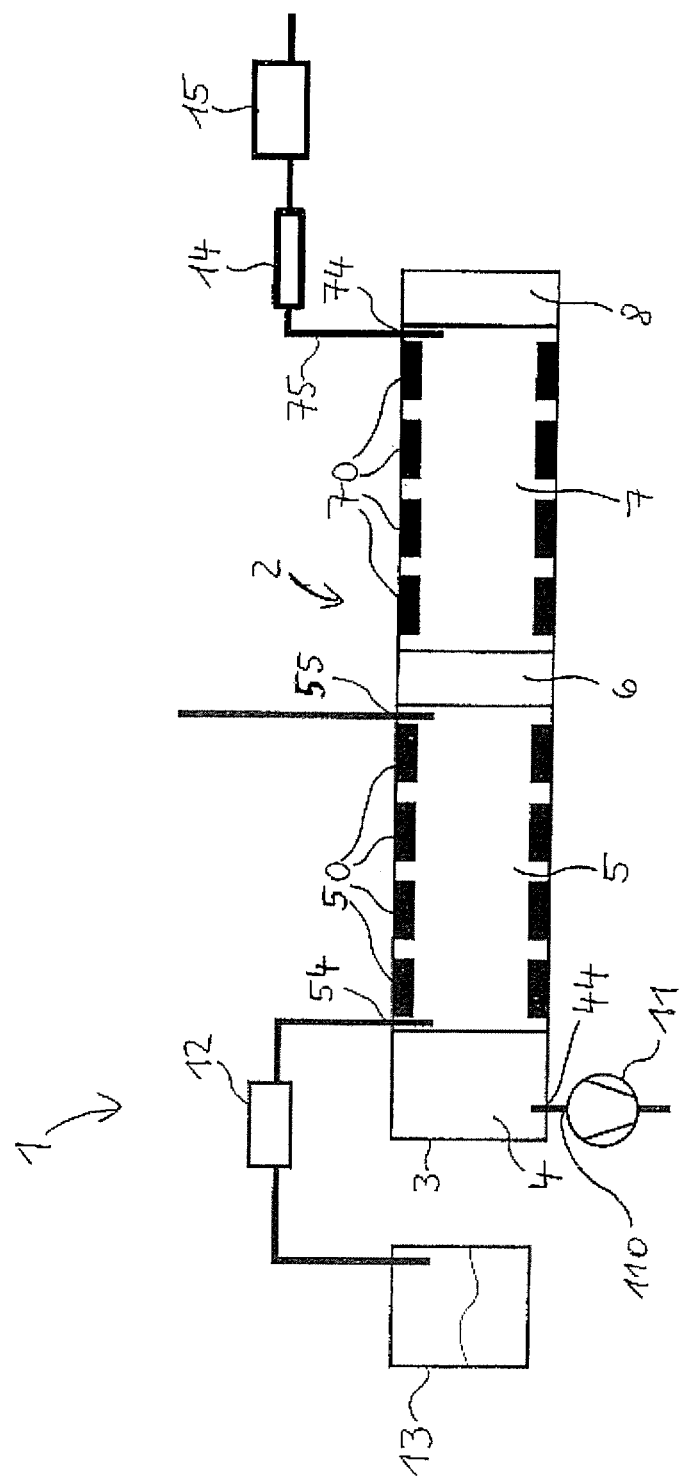

(51) Int. Cl.
*H01J 37/08* (2006.01)
*H01J 49/06* (2006.01)

(58) Field of Classification Search
CPC .. H01J 49/0431; H01J 49/044; H01J 49/0445;
H01J 49/06; H01J 49/061; H01J 49/067;
H01J 49/08; H01J 49/10; H01J 49/145;
H01J 49/162; H01J 49/42; H01J 49/4225;
H01J 37/08
USPC ....... 250/281, 282, 287, 286, 288, 292, 294,
250/290, 293, 283, 289, 396 R, 423 P,
250/423 R, 424, 298, 307, 311
See application file for complete search history.

(56) References Cited

U.S. PATENT DOCUMENTS

| | | | | |
|---|---|---|---|---|
| 4,551,624 A * | 11/1985 | Spangler | ............. | G01N 27/622 250/282 |
| 4,839,143 A * | 6/1989 | Vora | ............. | G01N 27/622 250/281 |
| 4,855,595 A * | 8/1989 | Blanchard | ............. | G01N 27/622 250/281 |
| 5,227,628 A * | 7/1993 | Turner | ............. | G01N 27/622 250/282 |
| 5,338,931 A * | 8/1994 | Spangler | ............. | H01J 49/162 250/287 |
| 5,552,600 A * | 9/1996 | Davies | ............. | G01N 27/622 250/286 |
| 6,649,907 B2 * | 11/2003 | Ebeling | ............. | H01J 49/044 250/288 |
| 6,690,004 B2 * | 2/2004 | Miller | ............. | G01N 27/624 250/282 |
| 7,034,292 B1 * | 4/2006 | Whitehouse | ............. | H01J 49/004 250/281 |
| 7,122,794 B1 * | 10/2006 | Miller | ............. | H01J 49/0013 250/281 |
| 7,170,052 B2 * | 1/2007 | Furutani | ............. | B82Y 10/00 250/281 |
| 7,170,053 B2 * | 1/2007 | Shvartsburg | ............. | G01N 27/624 250/282 |
| 7,244,931 B2 * | 7/2007 | Zimmermann | ............. | G01N 27/622 250/287 |
| 7,285,774 B2 * | 10/2007 | Guevremont | ............. | H01J 49/063 250/282 |
| 7,399,959 B2 * | 7/2008 | Miller | ............. | H01J 49/0018 250/281 |
| 7,541,576 B2 * | 6/2009 | Belov | ............. | H01J 49/0031 250/282 |
| 7,569,811 B2 * | 8/2009 | Javahery | ............. | H01J 49/066 250/282 |
| 7,812,305 B2 * | 10/2010 | Miller | ............. | G01N 27/624 250/281 |
| 8,071,938 B2 * | 12/2011 | Guharay | ............. | G01N 21/658 250/286 |
| 8,288,717 B2 * | 10/2012 | Park | ............. | G01N 27/622 250/281 |
| 8,502,138 B2 * | 8/2013 | Matthews | ............. | G01N 27/622 250/282 |
| 2005/0133716 A1 * | 6/2005 | Miller | ............. | G01N 27/624 250/293 |
| 2005/0205775 A1 * | 9/2005 | Bromberg | ............. | H01J 49/0031 250/290 |
| 2006/0022132 A1 * | 2/2006 | Zhang | ............. | H01J 49/145 250/290 |
| 2006/0027746 A1 * | 2/2006 | Guevremont | ............. | G01N 27/624 250/292 |
| 2006/0289745 A1 * | 12/2006 | Miller | ............. | G01N 27/624 250/294 |
| 2007/0040111 A1 | 2/2007 | Jill et al. | | |
| 2007/0075240 A1 * | 4/2007 | Hieke | ............. | H01J 49/04 250/282 |
| 2007/0114395 A1 * | 5/2007 | Swenson | ............. | G01N 27/622 250/292 |
| 2009/0108194 A1 * | 4/2009 | Page | ............. | H01J 49/066 250/282 |
| 2011/0036977 A1 * | 2/2011 | Denton | ............. | G01N 27/622 250/283 |
| 2011/0101214 A1 * | 5/2011 | Miller | ............. | G01N 27/624 250/282 |
| 2014/0084155 A1 * | 3/2014 | Li | ............. | H01J 49/061 250/288 |
| 2015/0168318 A1 * | 6/2015 | Beckman | ............. | H01J 49/0431 250/307 |

* cited by examiner

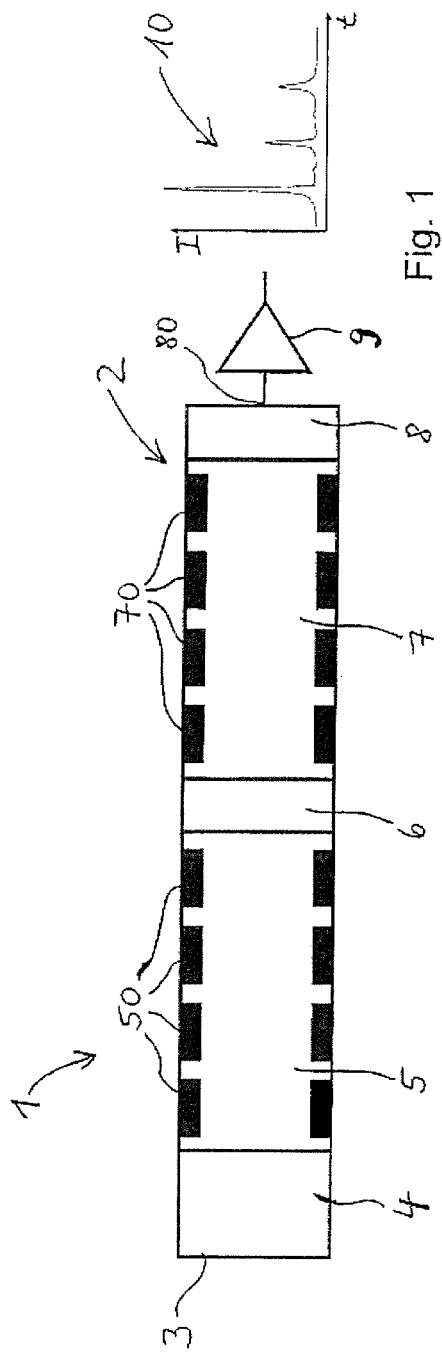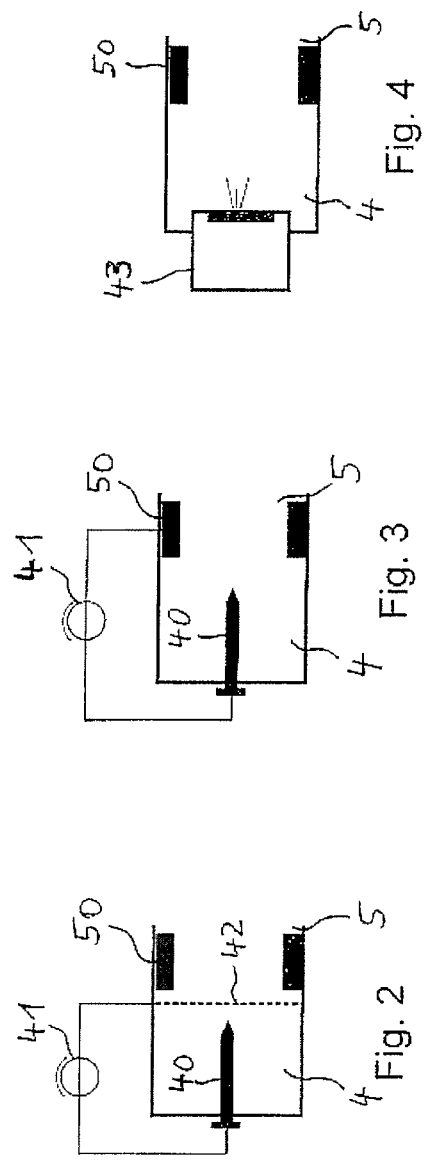

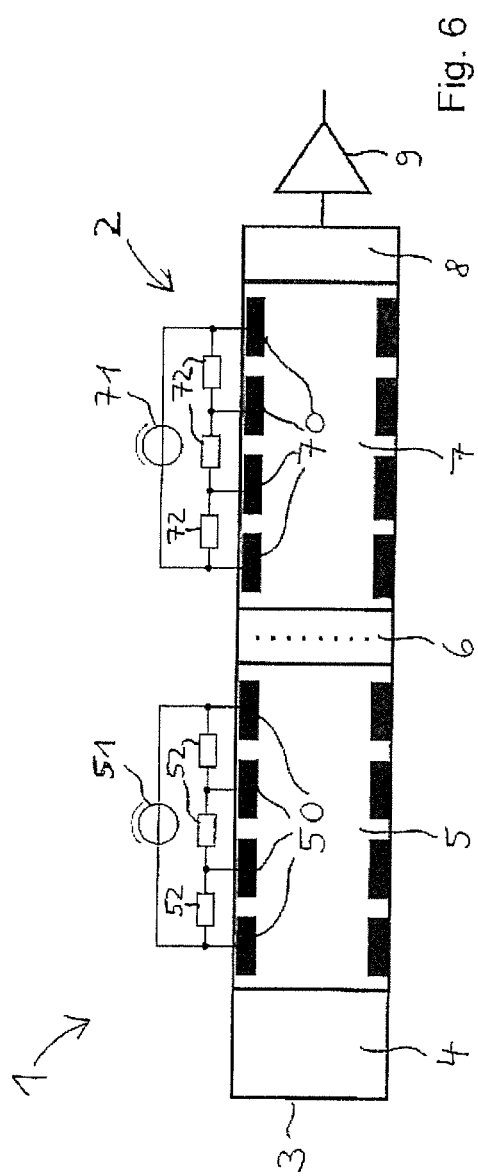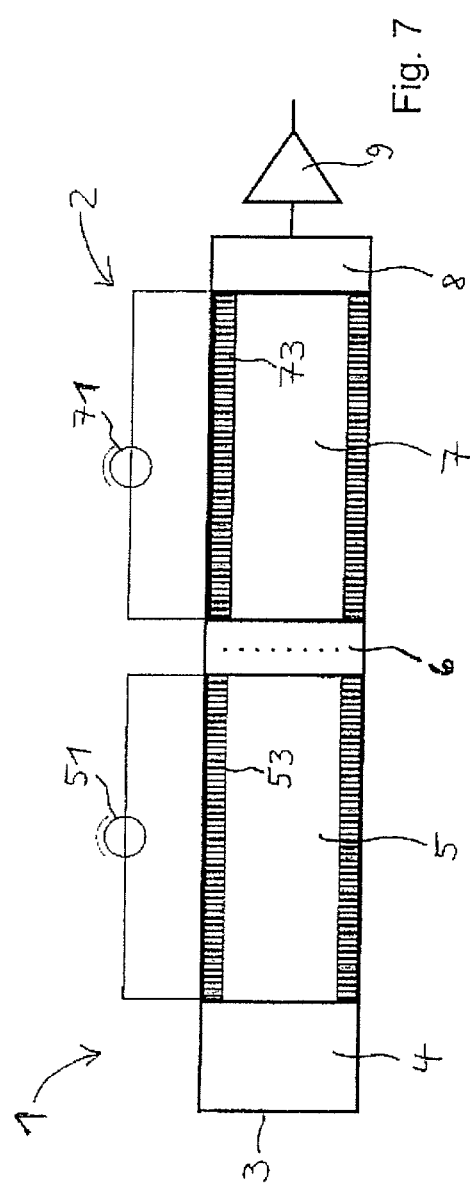

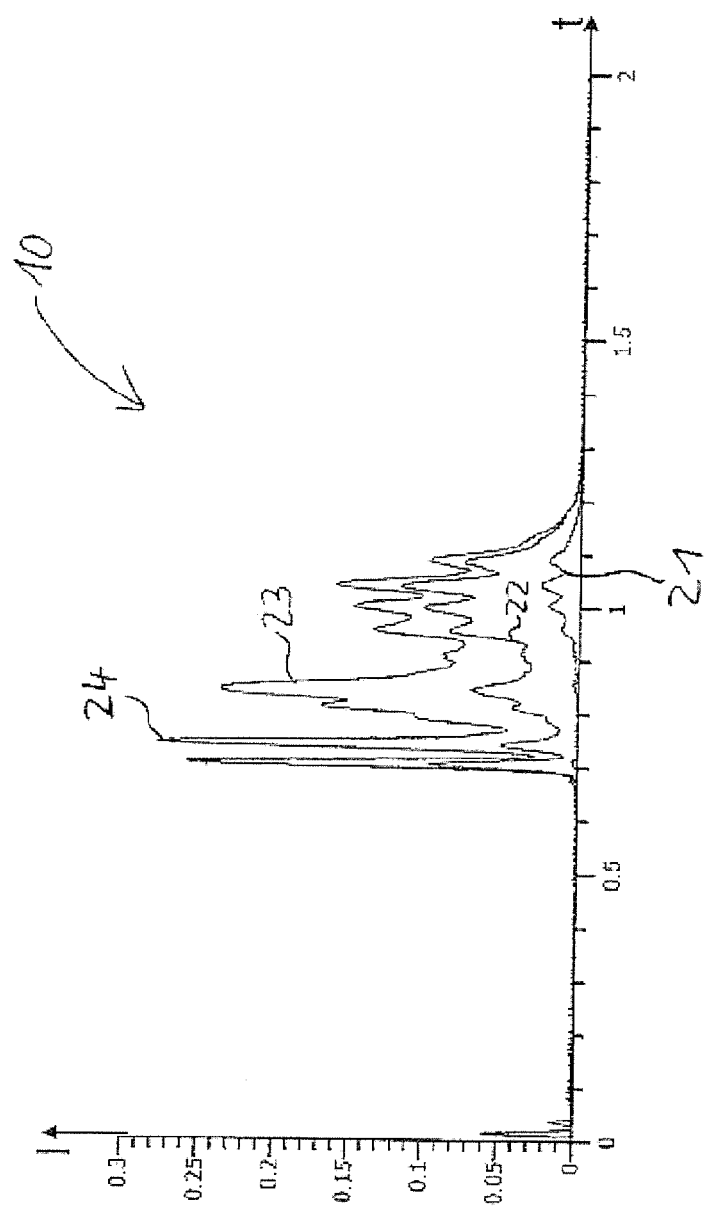

GAS ANALYZING DEVICE COMPRISING AN ION MOBILITY SPECTROMETER AND METHOD OF USING THE SAME

The invention relates to a gas analyzing device comprising at least one ion mobility spectrometer, as claimed in claim 1. The invention further relates to a method for analyzing gas by means of a gas analyzing device according to the ion mobility spectrometry method as claimed in claim 8.

The invention generally relates to the field of analysis of gaseous substances, with the term "gaseous substances" to be understood in the broadest sense and comprising in particular any substance mixtures. In such gaseous substances, particular substances present therein are to be detected in a qualitative and/or quantitative manner. For instance, in medical technology, for example for breath analysis, in safety technology or in the monitoring and control/regulation of chemical processes, there is an urgent need for cost-effective, compact, rapid and sensitive gas analyzing devices for analyzing the complex gas mixtures occurring therein. In the area of safety technology, the aim is, for example, to carry out a continuous monitoring of the concentration of different hazardous substances in the environment, such as, for example, toluene and the cancer-causing benzene, using portable measurement systems. Said substances toluene and benzene frequently occur together. Owing to the differing toxicity, the limit values for benzene are distinctly lower than for toluene. To date, a rapid detection of benzene in the presence of toluene or water using available portable measurement systems, for example ion mobility spectrometers, has not been possible.

An ion mobility spectrometer (IMS) has the advantage that it is a relatively small system which can be used successfully for the very rapid analysis of even complex gas mixtures and has the necessary low detection limits for a series of substances. An ion mobility spectrometer is, for example, described in U.S. Pat. No. 4,777,363. Unfortunately, the rapid detection of a multiplicity of substances of practical relevance in the case of use in substance mixtures or in the case of air moisture is not possible with known ion mobility spectrometers owing to cross-sensitivities. For example, this applies in the case of use for the monitoring of the benzene content of air in the presence of toluene or water vapor in a concentration of practical relevance. A necessary quantitative detection of many substances is not possible with a rapid system without prior chromatographic preseparation.

It is therefore an object of the invention to specify a gas analyzing device which is based on ion mobility spectrometry and which has relatively low cross-sensitivities for many gas constituents of practical relevance to be detected. Furthermore, it is intended that a corresponding method for analyzing gas be specified.

This object is achieved according to claim 1 by a gas analyzing device comprising at least one ion mobility spectrometer, wherein the gas analyzing device comprises an energy supply device which acts on a reaction chamber of the ion mobility spectrometer and which is geared to manipulating the density of free reactant ions in the reaction chamber by supply of energy. The free reactant ions are available to form analyte ions, with which the ion mobility spectrometry can then be carried out. In this connection, the word "free" means that the reactant ion is free of water molecules or other unwanted binding partners that are bound thereto. As a result of the specific supply of energy in the reaction chamber, it is possible for desired free reactant ions of the ion mobility spectrometry method to be cleared of the undesired binding partners thereof and/or for bonds of the desired reactant ions with undesired binding partners to be completely or partially suppressed. In this way, it is possible for the statistical probability of the binding of free reactant ions with an undesired binding partner in the reaction chamber and thus the density of free reactant ions of the ion mobility spectrometry method to be increased.

With respect to known pure ion mobility spectrometers, the gas analyzing device according to the invention is expanded by the energy supply device which acts on the reaction chamber of the ion mobility spectrometer. The energy supply device can be realized in different ways. The energy to be fed into the reaction chamber by means of the energy supply device can, for example, be supplied by irradiation of the reaction chamber with electromagnetic waves or by thermal radiation. The electromagnetic waves can, for example, be generated in the form of light within the visible wavelength range or within other wavelength ranges, for example within the microwave range. Advantageously, the supply of energy can also be effected with the aid of electric fields.

The energy supply device can be structurally integrated into the ion mobility spectrometer, for example the reaction chamber thereof, or be arranged externally thereof.

According to the invention, the gas analyzing device comprises a negative-pressure generation device which is coupled to a reaction chamber of the ion mobility spectrometer and which is geared to generating a negative pressure with respect to the atmospheric pressure at least in the reaction chamber. Accordingly, the ion mobility spectrometer has been modified at least to the effect that it comprises a reaction chamber operated with negative pressure. Known, self-sufficiently usable ion mobility spectrometers are, in contrast, operated at atmospheric pressure or a slight positive pressure in order, as a result of the positive pressure, to keep contaminants out of the inner chambers of the ion mobility spectrometer. In this connection, the negative-pressure generation device can be directly or indirectly, for example via another chamber of the ion mobility spectrometer, coupled to a reaction chamber. The negative-pressure generation device can fundamentally be of any construction type, for example in the form of a pump, for example a diaphragm pump, a rotary vane pump or some other pump, or in the form of a blower or of a compressor. In this connection, the negative pressure to be generated with respect to the atmospheric pressure does not need to attain an extremely large pressure difference in relation to the atmospheric pressure, especially not within the range of pressure values typically referred to as high vacuum, as is necessary for example in the case of a mass spectrometer. According to the invention, the negative-pressure generation device generates a negative pressure within the range from 2 mbar to 100 mbar (absolute pressure). This has the advantage that the gas analyzing device can be realized with simple cost-effective components. The negative-pressure generation device in particular can be realized with conventional products available on the market.

This development of the invention has the advantage that the particle density of the gas mixture situated in the reaction space is reduced as a result of the generation of the negative pressure in the reaction space. As a result of the reduction of the particle density, it is possible to increase the mean free path length which the particles can cover in the reaction chamber. This opens up the possibility of accelerating the particles in the reaction chamber between two collisions by means of supply of energy, for example by an electric field, such that undesired particle bonds can break up, by the particles being concentrated with energy as a result of acceleration such that the binding energy is exceeded. As a result, it is possible in the reaction chamber to provide desired free reactant ions for a chemical gas phase ionization in a relatively high concentration, i.e., reactant ions previously bound to undesired particles are cleared of the undesired particles at least to a relatively large extent or do not even form undesired bonds and are therefore provided in the desired pure reactant ion form. This improves the probability of the reactant ions reacting with gas constituents to be analyzed, the so-called analytes. Desired analyte ions can be generated in a relatively large amount by a chemical gas phase ionization, since the probability of ionization of many analytes is distinctly increased in the case of a high number of unbound reactant ions or the ionization is only possible in this form. As a result, it is possible to significantly increase the measurement sensitivity, i.e., the sensitivity, of the gas analyzing device for a multiplicity of analytes previously uncapturable in complex substance mixtures by means of an ion mobility spectrometer. The thus improved gas analyzing device is therefore suitable for a multiplicity of applications, such as, for example, the direct monitoring of the ambient air for toxic constituents, breath analysis in medical technology, the continuous quality control in the chemical industry, for example in the manufacture of fragrances, and in other areas such as, for example, safety technology.

In an exemplarily described method of operating an ion mobility spectrometer, an ionization source generates protonated water ions $H_3O^+$ (oxonium) as reactant ions, for example by ionization of the moisture present in the air. In the actual chemical gas phase ionization, the proton $H^+$ shall then be released in the reaction chamber to the analytes having higher proton affinity than the oxonium and thereby ionize the analytes. This gives rise to the analyte ions, which are then analyzed in the further course of the ion mobility spectrometry. Besides the aforementioned desired ionization process, there are also competing, undesired ionization processes, consuming the reactant ions or making them less suitable for the desired ionization processes, since they are no longer available for an ionization for many analytes in this form. The air humidity always occurring in practical applications leads to a formation of water clusters $(H_3O^+)(H_2O)_n$ where n=1, 2, 3 . . . . These lead to a suppression of the desired ionization via the pure reactant ions. Moreover, the simultaneous presence of analytes having different proton affinities leads to competing ionization processes, and this leads to other substances being "masked". As a result, the amount of free reactant ions which are available for ionization of the analytes and are unbound to water molecules or other analytes is reduced such that the sensitivity for a measurement of a further substance having lower proton affinity decreases and a capture is frequently not possible. Using the gas analyzing device according to the invention, it is possible, owing to the additional, reaction chamber-generated energy transfer to the reactant ions with an appropriate combination of high field strength and mean free ion path length arising from the gas pressure, to increase the density of free reactant ions unbound to water molecules or other analytes.

Using the gas analyzing device according to the invention, very rapid measurements and thus a rapid repetition of measurements are possible without the need for a chromatographic preseparation of the gas mixture to be analyzed. Measurements can, for example, be carried out at a frequency of 500 Hz. The gas analyzing device according to the invention can therefore be used for a real-time gas analysis.

Because of the high repetition rate of the measurements that is possible, an averaging can also take place over multiple measurement cycles in order to improve the output signal, especially the signal-to-noise ratio.

The desired supply of energy to the reactant ions in the reaction chamber in order to suppress or separate the undesired bonds can, for example, be achieved by generating an electric field in the reaction chamber. Since even the undesirably bound molecules, the so-called water clusters, are present as ions, these are accelerated by the electric field. According to an advantageous development of the invention, it is therefore envisaged that the gas analyzing device comprises, as energy supply device, a first field generation device which is geared to generating an electric field in the reaction chamber. As a result, the ion mobility spectrometer is further modified in comparison with known ion mobility spectrometers by the first field generation device being added. Because of the negative pressure formed in the reaction chamber, it is possible in conjunction with the electric field to achieve a very efficient separation of the water clusters, and so a large number of desired pure reactant ions is then available. The electric field can, for example, have field strengths within the range from 30 to 100 V per millimeter. Water clusters which have formed dissociate under these conditions in the reaction chamber. Because of the high kinetic energies, the probability of a new formation of water clusters is moreover considerably reduced. This is therefore possible because the energy incorporated in the electric field exceeds the binding energy of relatively large water clusters and the existing hydrogen bonds are thus broken. Therefore, the density of free reactant ions increases on average. This allows a simultaneous ionization of different analytes because competing ionization processes are of no consequence owing to the high density of pure reactant ions up to a particular concentration range of the analytes. Furthermore, a direct analysis of gaseous samples having high air moisture is therefore also possible.

The first field generation device can be arranged on or in the reaction chamber, or at least in the region of the reaction chamber such that the desired electric field can be generated in the reaction chamber. The first field generation device can be geared especially to generating an electric field having a potential gradient from an ionization-source-sided region of the reaction chamber toward an ion gate.

The field profile present in the reaction chamber can be altered systematically, forming different densities of free and water-bound reactant ions. This makes it possible to carry out an analysis at a high repetition rate under different chemical ionization conditions, and, as a result, further information can be obtained, especially about the proton affinity of the various substances in the gas mixture to be analyzed.

The gas analyzing device and especially the ion mobility spectrometer thereof can, aside from the explained modifications, be otherwise constructed like known ion mobility spectrometers. More particularly, the gas analyzing device or the ion mobility spectrometer thereof can comprise at least the following components:

a) an ionization source region having an ionization source,
b) the reaction chamber coupled to the ionization source region,
c) a drift chamber comprising a drift gas supply connector connected to a gas supply line for supplying drift gas into the drift chamber,
d) a switchable ion gate between the reaction chamber and the drift chamber, e) an ion detector at the end of the drift chamber that is facing away from the ion gate, f) a second field generation device which is geared to generating an electric field in the drift chamber.

The second field generation device can be arranged on or in the drift chamber, or at least in the region of the drift chamber such that the desired electric field can be generated in the drift chamber. The second field generation device can be geared especially to generating an electric field having a potential gradient from the ion gate toward the ion detector.

The first and/or the second field generation device can, for example, comprise electrodes arranged in succession in the direction of the desired potential gradient of the electric field to be generated, for example ring electrodes arranged in the reaction chamber or the drift chamber. The first and/or the second field generation device can also be formed with an individual electrode extending lengthwise in the direction of the desired potential gradient, which electrode has been produced from a material having a relatively high specific resistance, for example in the form of a single ring electrode. Because of the relatively high resistance value, the desired electric field can also be generated in the longitudinal direction, i.e., in the desired direction of movement of the ions. For instance, such a single ring electrode can, for example, be formed by a cylinder composed of conductive glass. The first and/or the second field generation device can also comprise combinations of the abovementioned types of electrodes.

The ion gate serves as a temporary barrier for the analyte ions on their way from the reaction chamber to the drift chamber. The ion gate is, for example, operated in a pulsed manner according to a certain temporal pattern such that it is opened and closed and, in the opened phases, analyte ions enter the drift chamber from the reaction chamber. As a result, it is possible to specify defined, separate measurement cycles of the gas analyzing device in line with the switching cycle of the ion gate.

The ion gate can be formed in line with the ion gates in known ion mobility spectrometers, for example with two electrodes arranged in succession in the direction of movement of the analyte ions or electrodes arranged interconnected to one another in one plane. According to an advantageous development of the invention, the ion gate comprises at least three electrodes arranged in succession in the direction from the reaction chamber to the drift chamber. The electrodes are connectable or permanently connected with different electric potentials. According to an advantageous development of the invention, the middle electrode of the ion gate can be switchable in terms of potential by means of an electric switching mechanism of the gas analyzing device. By means of the switching mechanism, the middle electrode can therefore be switched from one electric potential to another electric potential. Such an ion gate is highly efficient with respect to the barrier action. A further advantage is that, as a result of the three electrodes arranged in succession, the electrodes adjacent to one another can in each case be operated in pairs with an electric field having a field strength which corresponds to the field strength in the adjacent chamber, i.e., the reaction chamber, on the one hand, and the drift chamber, on the other. This has in turn the advantage that, as a result of the switching of the ion gate between the blocked and the opened state, the existing electric fields in the reaction chamber and the drift chamber can be left largely unaffected. The electrodes of the ion gate can, for example, be formed as ring electrodes or as lattice electrodes.

According to an advantageous development of the invention, the negative-pressure generation device is geared to generating a drift gas stream against the drift direction of the ions in the drift chamber. This has the advantage that the drift gas necessary in any case for carrying out the ion mobility spectrometry can be guided through the drift chamber without the need for additional components. On the contrary, the negative-pressure generation device can be concomitantly used for this purpose. The drift gas stream that is generated constantly supplies fresh drift gas and counteracts a contamination of the drift chamber by undesired particles, since the drift gas stream leads to a flushing of the drift chamber. In this connection, the drift gas can be purified and dried by filters.

The negative-pressure generation device can fundamentally be connected to various points of the gas analyzing device or of an enclosure body of the ion mobility spectrometer. In an advantageous configuration of the invention, the reaction chamber can be pressure-connected to the drift chamber, i.e., there is an equalization of pressure between the reaction chamber and the drift chamber. As a result, the prevailing pressure in the reaction chamber and in the drift chamber is substantially identical, aside from small pressure differences occurring due to flow effects. For instance, the negative-pressure generation device can, for example, be connected to a suck-off connector of the gas analyzing device.

According to an advantageous development of the invention, the negative-pressure generation device comprises a suction connector connected to a suck-off connector of the gas analyzing device, which suck-off connector is arranged in front of the ion gate in the drift direction of the ions. For instance, the suck-off connector can, for example, open into the reaction chamber or into the ionization source region. This has the advantage that the drift gas stream can also be guided in full or in part through the reaction chamber. As a result, the reaction chamber can also be purified of undesired particles. This in turn benefits the sensitivity and measurement accuracy of the gas analyzing device.

According to an advantageous development of the invention, the gas analyzing device comprises a mass flow regulator which is geared to supplying the drift gas and is connected to the drift chamber. This has the advantage that a precisely adjustable, constant stream of drift gas can be supplied to the gas analyzing device. However, the drift gas stream can also be set and held via a constant flow restriction at a known pressure difference, simplifying the structure of the system.

According to the invention, the gas analyzing device comprises at least one heating device which is geared to heating the reaction chamber and/or the drift chamber. The heating device can be operated especially via a temperature regulator in order to keep the temperature in the reaction chamber or the drift chamber constant. By means of such a specific heating, it is, for example, possible to further reduce the response times of the gas analyzing device for strongly absorbing gases. Furthermore, it is possible via a heater to also increase the kinetic energy of the collisions of the gas particles both in the reaction chamber and in the drift chamber, leading to an advantageous reduction of unwanted bonds of the reactant ions. Furthermore, a defined temperature adjustment of the structure prevents an impact of the ambient temperature on the ion mobility and on other temperature-dependent variables.

The object mentioned at the beginning is also achieved according to claim 8 by a method for analyzing gas by means of a gas analyzing device according to the ion mobility spectrometry method, wherein the density of free reactant ions of the ion mobility spectrometry method in the reaction chamber is manipulated by supply of energy by means of an energy supply device acting on a reaction chamber of the ion mobility spectrometer in order to clear desired free reactant ions of the undesired binding partners thereof and/or to completely or partially suppress bonds of the desired reactant ions with undesired binding partners. Using the method, it is possible to achieve the same advantages as described above for the gas analyzing device. To carry out the method, it is possible to use especially a gas analyzing device of the type described at the beginning.

According to the invention, ionized particles already present in the reaction chamber are accelerated by an electric field such that desired reactant ions of the ion mobility spectrometry method are cleared of the undesired binding partners thereof and/or bonds of the desired reactant ions with undesired binding partners are completely or partially suppressed. For instance, the supplied kinetic energy breaks, for example, the hydrogen bonds of the water clusters described at the beginning. It is also possible to suppress undesired bonds from the outset, though there is generally no one-hundred-percent suppression, but at least a distinct reduction in the frequency of undesired bonds. For example, this can be achieved by accelerating ionized particles already present in the reaction chamber by an electric field such that their kinetic energy exceeds the binding energy between desired reactant ions of the ion mobility spectrometry method and undesired particles. The electric field in the reaction chamber can, for example, be generated by the energy supply device in the form of the mentioned first field generation device.

According to the invention, an electric field is generated in the reaction chamber and in the drift chamber in the desired drift direction of the ions in the drift chamber. Owing to the electric field in the reaction chamber, there is an acceleration of the ions present therein, and the above-described breaking of the bonds of the desired reactant ions is achieved as a result. Because of the relatively high mean free path length generated by the negative pressure, a comparatively weak electric field, for example having field strengths within the range from 30 to 100 V per millimeter, is enough for the desired effect and thus a distinct increase in the free, non-water-bound reactant ions available for a reaction with analyte substances with slight proton affinity.

According to the invention, at least the reaction chamber is subjected to application of a negative pressure with respect to the atmospheric pressure during the operation of the gas analyzing device.

According to an advantageous development of the invention, gas to be analyzed is sucked into the reaction chamber through an analyte inlet connector of the gas analyzing device by means of the negative pressure in the reaction chamber. The negative pressure generated can therefore be utilized for a further function, viz., supplying the gas to be analyzed into the gas analyzing device. As a result, it is especially possible to supply a constant stream of gas to be analyzed to the gas analyzing device.

According to an advantageous development of the invention, a drift gas is introduced into the drift chamber and, owing to the negative pressure in the reaction chamber, guided through the drift chamber against the drift direction of the ions.

According to an advantageous development of the invention, a drift gas mass flow is fed into the drift chamber in a regulated manner. This has the advantage that a precisely adjustable, constant stream of drift gas can be supplied to the gas analyzing device.

According to an advantageous development of the invention, water vapor or some other makeup gas is fed into the reaction chamber. As a result, the amount of possible reactant ions can be further increased or varied. Owing to the high density of free reactant ions thus existing in the reaction chamber, various analytes can be ionized at the same time and it is possible to counteract a masking of substances. Furthermore, the influence of the air humidity present in the sample gas can be distinctly reduced and a direct detection of substances having proton affinities below those of water clusters in the moist sample gas mixture can be made possible in the first place. Possible makeup gases include especially those gases which make it possible to generate an altered proton affinity, for example ammonia.

According to an advantageous development of the invention, the supply of energy in the reaction chamber is systematically altered in order to obtain information about the ionizability of the substances to be analyzed with reactant ions which are bound to varying extents. The field profile present in the reaction space can be systematically altered, forming different densities of free and water-bound reactant ions. As a result, it is possible to carry out an analysis at a high repetition rate under different chemical ionization conditions, making it possible to obtain further information especially about the proton affinity of the various substances in the gas mixture to be analyzed.

The gas analyzing device according to the invention can be especially advantageously used with the following operating parameters. The method according to the invention for analyzing gas can also be operated accordingly. The field strength specified here is the field strength of the electric field, as generated by the first field generation device, in the reaction chamber. The drift chamber can be operated with comparable field strengths. The pressure values specify the absolute pressure generated in the reaction chamber by the negative-pressure generation device.

Advantageously, a field strength is within the range from 12.5 V/cm per mbar absolute pressure to 37.5 V/cm per mbar absolute pressure. In this connection, the absolute pressure concerns the selected negative pressure which the negative-pressure generation device generates in the reaction chamber.

It is possible here to use a desired nominal value of the negative pressure generated by the negative-pressure generation device in order to determine the field strength to be adjusted. The negative pressure generated by the negative-pressure generation device can, for example, be monitored by means of a pressure sensor. A pressure regulation in order to achieve a constant value of the absolute pressure of the reaction chamber can be carried out dependent on the value determined by the pressure sensor. Alternatively or additionally, the field strength can also be updated by automatic controlling of the first field generation device or of its voltage source dependent on the actual value of the absolute pressure, as captured by the pressure sensor. In the case of a pressure value deviating in an upward direction from the desired nominal value of the absolute pressure, the field strength can be increased accordingly; in the case of a pressure value deviating in a downward direction, it can be reduced accordingly.

Advantageously, the ion mobility spectrometer is operated in this connection at room temperature, for example within the range from 15° C. to 30° C., for example at 20° C. However, in particular applications, it may also be advantageous to heat the system, at least the ion mobility spectrometer, for example to a temperature within the range from 30° C. to 70° C. or from 70° C. to 200° C. Generally, a temperature range from 15 to 200° C. is therefore advantageous.

More particularly, it is possible, under these operating conditions depending on the selected absolute pressure in the reaction chamber (specified below in mbar), to adjust field strength values of the electric field in the reaction chamber within the following ranges.

| | |
|---|---|
| At 2 mbar: | 25 V/cm to 75 V/cm |
| At 10 mbar: | 125 V/cm to 375 V/cm |
| At 20 mbar: | 250 V/cm to 750 V/cm |
| At 50 mbar: | 625 V/cm to 1875 V/cm |

At 100 mbar: 1250 V/cm to 3750 V/cm

Figure 12:
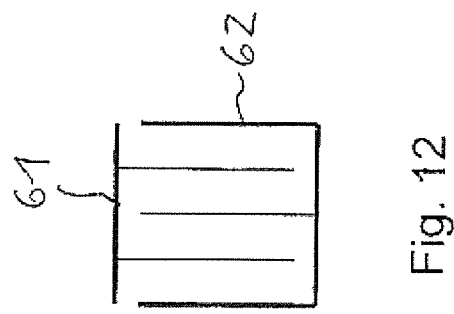
Figure 13:
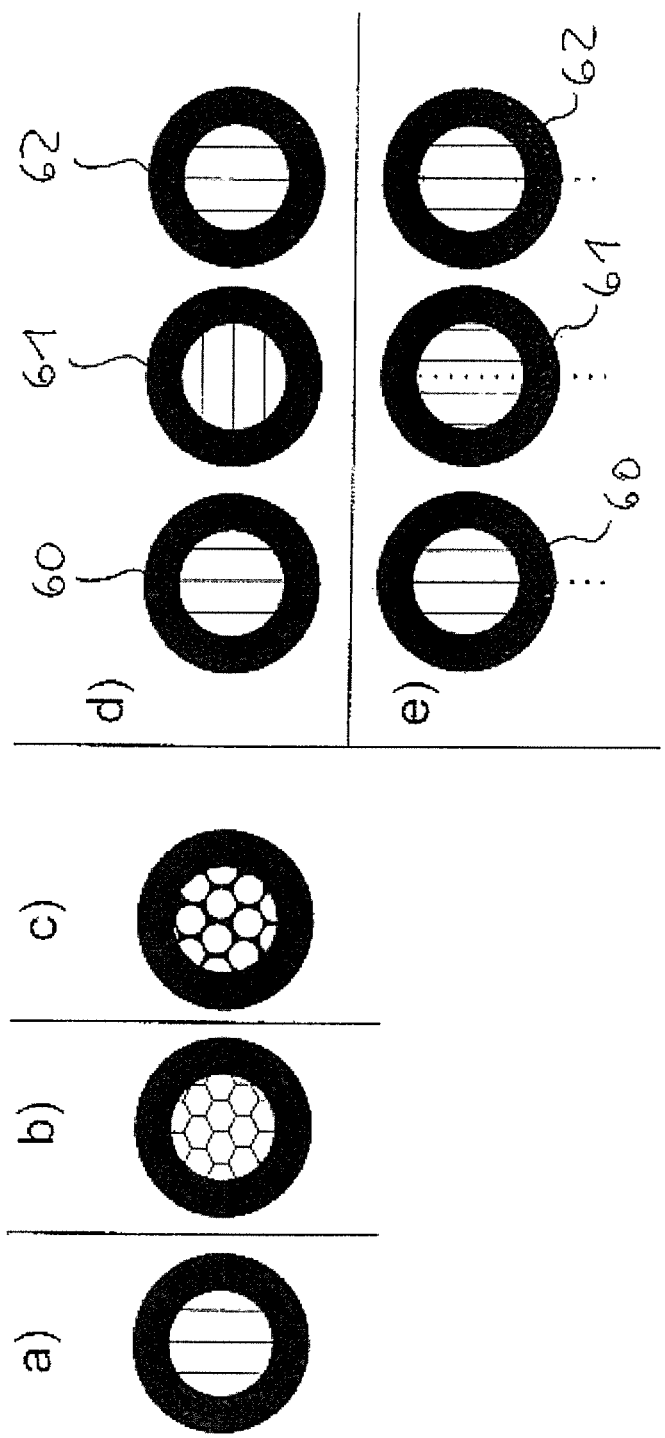
Figure 14:
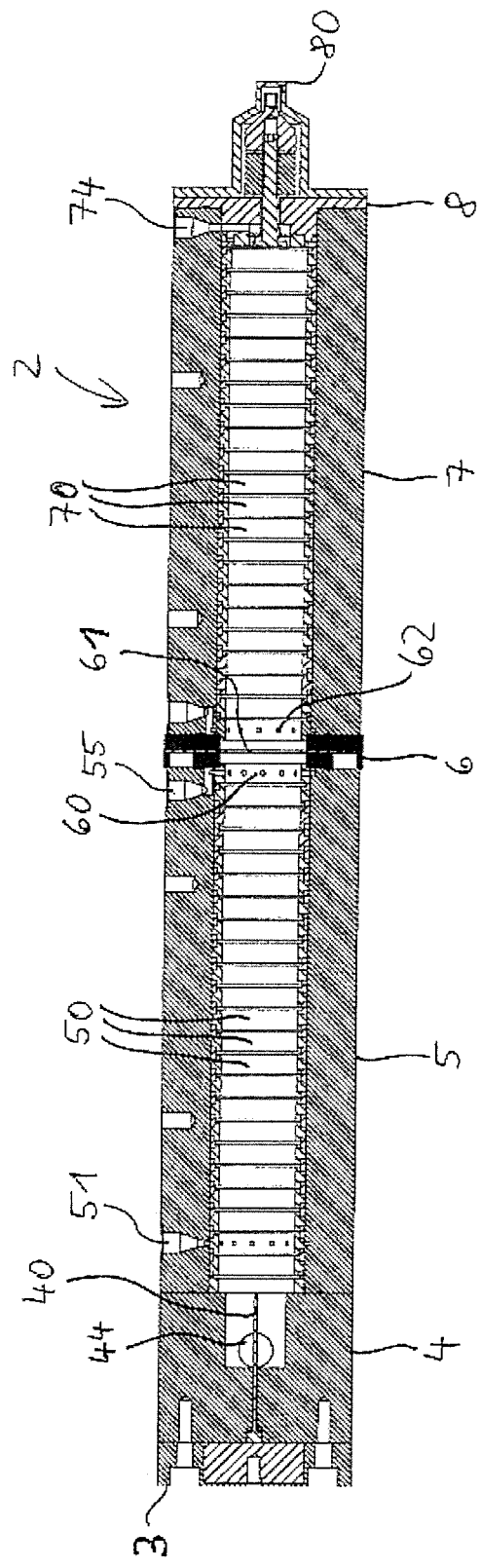

The invention will now be more particularly elucidated on the basis of exemplary embodiments with use of drawings, in which:

FIG. 1 shows the principle structure of a gas analyzing device in schematic form and FIGS. 2 to 4 show, as extracts, the region of the gas analyzing device that is depicted on the left-hand side of FIG. 1, with various embodiments of an ionization source and FIG. 5 shows the gas analyzing device according to FIG. 1 with further components and FIGS. 6 and 7 show the gas analyzing device according to FIG. 1 with different embodiments of field generation devices and FIGS. 8 to 12 show, as extracts, the middle region of the gas analyzing device according to FIG. 1 with different embodiments of an ion gate and FIG. 13 shows different embodiments of electrodes of the ion gate and FIG. 14 shows a constructive embodiment of an ion mobility spectrometer in a sectional side view and FIG. 15 shows a spectrogram generated using the gas analyzing device.

In the figures, the same reference signs are used for elements corresponding to one another.

In general, it should be additionally pointed out that FIGS. 1 to 4 and 6 to 12 show the gas analyzing device or the ion mobility spectrometer thereof with respect to the structure and the electrical circuitry, whereas FIG. 5 shows the same subject matter with respect to the connections of the pressure lines and with respect to the supply of the gases and other substances. The described gas analyzing device always comprises a combination of electrical circuitry and the connections depicted in FIG. 5, though the combination is not displayed in order to give a better overview.

The gas analyzing device 1 depicted in FIG. 1 comprises an ion mobility spectrometer 2 which has a, for example, pipe-shaped or tube-shaped enclosure body 3. The enclosure body 3 is divided into an ionization source region 4, a reaction chamber 5, an ion gate 6, a drift chamber 7 and an ion detector 8, which are arranged in succession in the abovementioned order as depicted in FIG. 1. The ion detector 8, which, for example, can be formed as a Faraday detector, for example in cup form or in the form of a metal plate, is connected to an amplifier 9 connected to an electrical connector 80 of the ion mobility spectrometer 2. The amplifier 9 amplifies the electric current supplied via the connector 80 and generated by the charges of the ions, yielding a spectrogram 10 at the output of the amplifier 9.

FIG. 1 further shows that electrodes 50, 70 of a first and, respectively, second field generation device are arranged in the reaction chamber 5 and in the drift chamber 7. In the exemplary embodiment depicted, the electrodes 50, 70 are formed as ring electrodes, which form a ring within the reaction chamber 5 and the drift chamber 7, respectively.

By means of FIGS. 2 to 4, various embodiments of the ionization source region 4 of the gas analyzing device 1 according to FIG. 1 will be first explained. FIG. 2 shows an ionization with the aid of a corona discharge in point-to-plane geometry. In this case, a corona needle 40, which is inserted into the ionization source region 4 at the left end face of the enclosure body 3, is connected via an electrical line to a voltage source 41 which provides a corona voltage. The voltage source 41 is electrically connected with its other connector to a lattice electrode 42, which is arranged within the enclosure body 3 in the ionization source region 4. A corona discharge is generated between the corona needle 40 and the lattice electrode 42, which discharge leads to an ionization of the gas molecules present therein.

In the embodiment of the ionization source region 4 according to FIG. 3, there is no lattice electrode 42 provided. Instead, the voltage source 41 is connected to the ring electrode 50 of the reaction chamber 5 that is closest to the ionization source region 4 and also to the corona needle 40. In this way, it is possible to achieve an ionization with the aid of a corona discharge in point-to-ring geometry.

In the embodiment of the ionization source region 4 according to FIG. 4, an electron emitter 43 is arranged in the ionization source region 4, which emitter likewise makes it possible to carry out an ionization of the gas.

The ionization source of the gas analyzing device 1 can be operated in a continuous manner or in a pulsed manner.

FIG. 5 shows various further components of the gas analyzing device 1 that are connected to the enclosure body 3 of the ion mobility spectrometer 2 via empty lines. A suck-off connector 44, which is arranged on the enclosure body 3 in the ionization source region 4, but can also be arranged, for example, in the region of the reaction chamber 5, is connected to a suction connector 110 of a negative-pressure generation device 11, for example a pump.

The water molecules required for the ionization in the ionization source region 4 can, for example, originate by means of air moisture from ambient air introduced into the gas analyzing device. Especially in the case of relatively dry air, additional water can be conducted into the enclosure body 3 from a water tank 13 via a water supply connector 54, for example directly into the reaction chamber 5. The water, for example in the form of water vapor, can be supplied directly from the water tank 13 via an empty line connected to the water supply connector 54, or, as depicted in FIG. 5, via a mass flow regulator 12 connected therebetween. By means of the mass flow regulator 12, it is possible to adjust the supply of water in a defined manner and to keep it constant.

The enclosure body 3 further comprises an analyte inlet connector 55 for supplying the analyte, i.e., the sample gas to be analyzed from the environment. The analyte inlet connector 55 can, for example, open into the reaction chamber 5, especially at the end of the reaction chamber 5 that is facing ion gate 6.

The enclosure body 3 further comprises a drift gas supply connector 74, which is connected to a drift gas reservoir via an empty line. As drift gas, it is fundamentally possible to use various gases which behave in a chemically/physically neutral manner with the analyte ions, such as, for example, nitrogen or a noble gas. Because of the relatively high nitrogen content of the ambient air, this can also be used directly as drift gas, and so FIG. 5 merely depicts a connection to the ambient air. A mass flow regulator 15 can be connected upstream of the drift gas supply connector 74, making it possible to regulate the supply of the drift gas and to keep it constant. A filter 14 can be further connected upstream of the drift gas supply connector 74, this being advantageous especially when using ambient air as drift gas, for cleaning said gas.

The ionization source region 4, the reaction chamber 5, the region of the ion gate 6 and the drift chamber 7 can be pressure-connected among each other, i.e., there is an equalization of pressure among these segments of the enclosure body 3. For instance, by means of the negative-pressure generation device 11, it is possible to generate the desired negative pressure and, while this is being done, to simultaneously suck in sample gas through the analyte inlet connector 55 and drift gas through the drift gas supply connector 74. All gases that have been sucked in are then sucked away and discharged via the negative-pressure generation device 11.

FIG. 6 shows the electrical circuitry of the reaction chamber 5 and of the drift chamber 7 for generating an electric field having a potential gradient in the longitudinal direction of the enclosure body 3, i.e., from left to right. For example, the ring electrodes 50 depicted can be connected to a voltage source 51 via a voltage divider circuit constructed from resistors 52. Correspondingly, the electrodes 70 can be connected to a voltage source 71 via a voltage divider circuit constructed from resistors 72. The first field generation device, which is assigned to the reaction chamber 5, therefore comprises not only the electrodes 50, but also the voltage source 51 and the resistors 52. The second field generation device assigned to the drift chamber 7 comprises not only the electrodes 70, but also the voltage source 71 and the resistors 72.

FIG. 7 shows an alternative embodiment of the first and of the second field generation device, in which continuous, nonstop electrodes 53, 73 are provided in each case instead of the ring electrodes, for example in the form of cylinders composed of conductive glass. In this case, the above-explained external voltage divider circuits can be omitted, since there is already a continuous voltage division owing to the relatively high specific resistance of the electrodes 53, 73.

Figure 8:
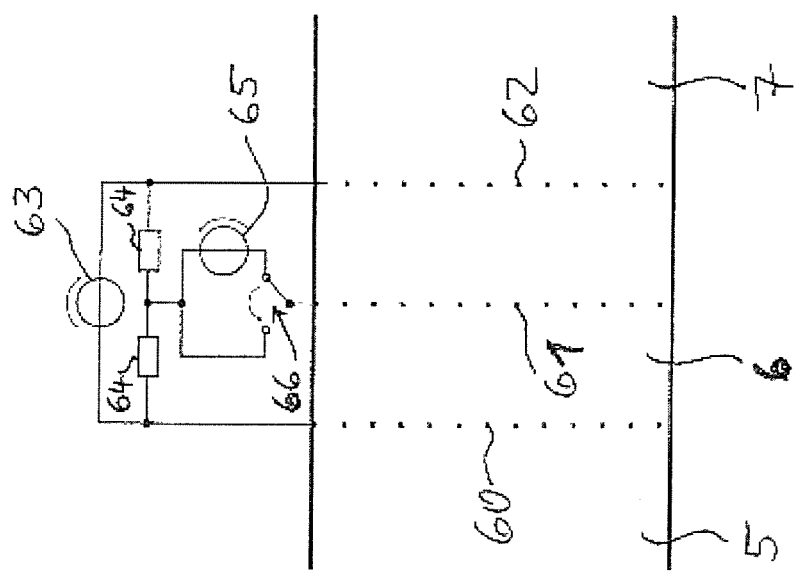

FIG. 8 shows a first embodiment of the ion gate 6 having three electrodes 60, 61, 62, which are arranged in succession in the direction from the reaction space 5 toward the drift chamber 7, for example about 450 micrometers apart. The electrodes 60, 61, 62 can likewise be formed as ring electrodes, like the electrodes 50, 70, or, as indicated in FIG. 8, as lattice electrodes. In this connection, the outer electrodes 60, 62 are each connected to a first ion-gate voltage source 63, which provides a gate voltage. The middle electrode 61 is, by means of an operable switching mechanism 66, for example a semiconductor switch or an arrangement of semiconductor switches, alternately connectable to a voltage potential generated from the gate voltage by resistors 64 of a voltage divider or to a voltage potential shifted with respect to said voltage potential by a block voltage. The block voltage is provided by a second ion-gate voltage source 65. If the operable switching mechanism 66 is in the switching state depicted in FIG. 8, the block voltage of the second ion-gate voltage source 65 is therefore effective, leading to a blocking of the ion gate. In this state, the ions in the reaction chamber 5 are prevented from entering the drift chamber 7. As a result of switching to the second depicted switching position of the switching mechanism 66, the ion gate can be opened. In this state, the ions migrate from the reaction chamber 5 to the drift chamber 7.

Figure 9:
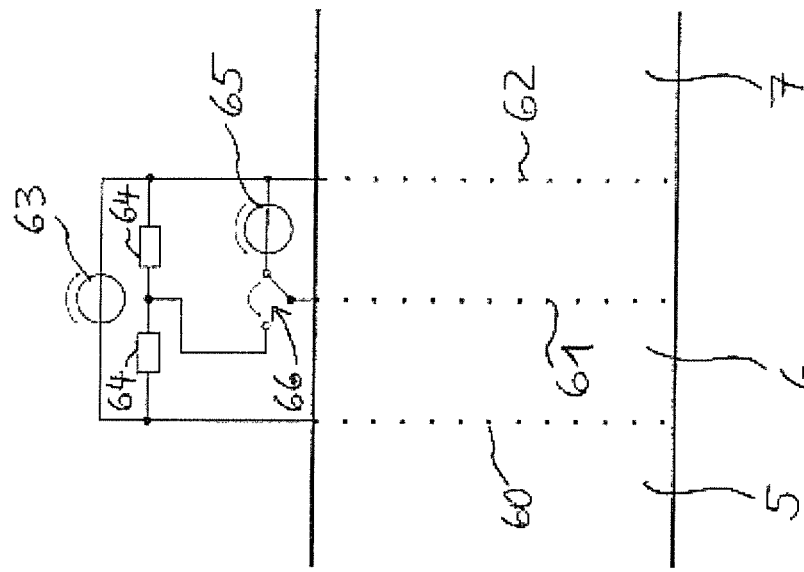

FIG. 9 shows an alternative embodiment of the ion gate 6, in which the electrical circuitry of the second ion-gate voltage source 65 is altered in comparison with FIG. 8 to the effect that the second ion-gate voltage source 65 is now directly connected with one of its connectors to the electrode 62, whereas the other connector is connected as before to the switching mechanism 66. In this way, the block voltage and the gate voltage have the same reference potential.

Figure 10:
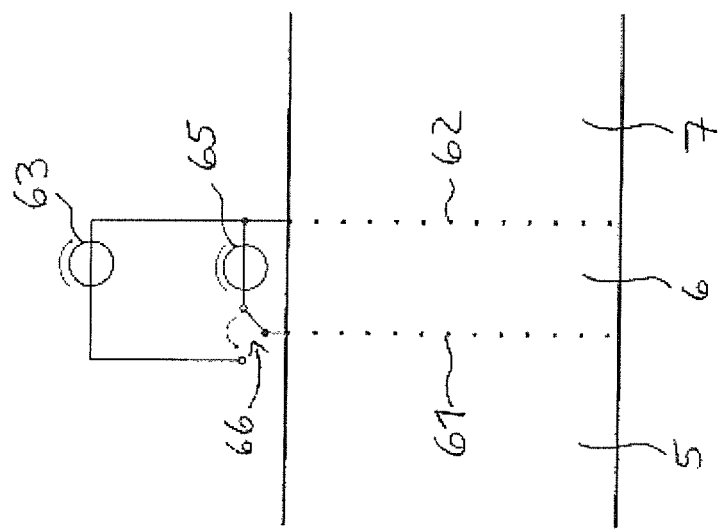

FIG. 10 shows one embodiment of the ion gate 6, in which only two electrodes 61, 62 are present. By means of a switching mechanism 66, it is possible to switch the potential effective at the left electrode 61 from the first ion-gate voltage source 63 to the second ion-gate voltage source 65. The right electrode 62 is connected to both voltage sources 63, 65.

Figure 11:
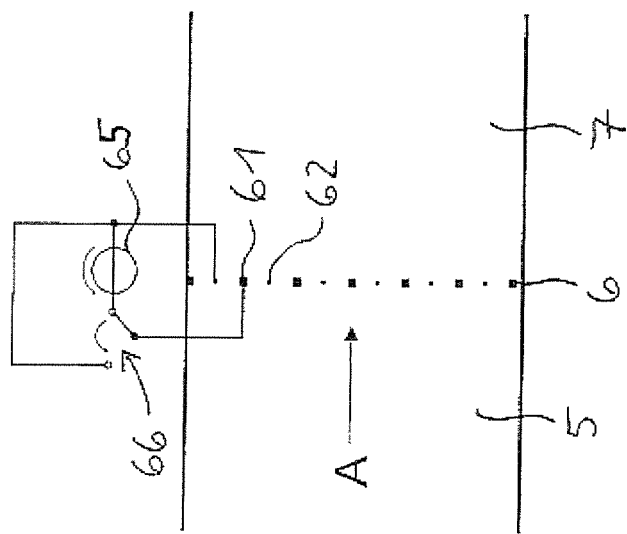

FIG. 11 shows one embodiment of the ion gate 6, in which an interdigital embodiment of the electrodes 61, 62 has been realized. The electrodes 61, 62 are situated in the same plane and are arranged interlocking into each other, as depicted in FIG. 12, which shows one view of the electrodes 61, 62 in the viewing direction A of FIG. 11. In the embodiment according to FIG. 11, only a single voltage source 65, which provides the block voltage, is present. By means of an operable switching mechanism 66, the electrode 61 can be alternately connected to the voltage source 65 or directly to the other electrode 62.

FIG. 13 shows, in views a), b) and c), various electrode forms of lattice electrodes, as can be used as electrodes 60, 61, 62. According to embodiment a), the electrode comprises strip-shaped conductors, which can extend vertically, horizontally or diagonally. According to embodiment b), the electrode comprises a hexagonal structure of the conductors. According to embodiment c), the electrode comprises a conductor arrangement having circular cutouts.

View d) shows the three aforementioned electrodes 60, 61, 62 next to one another. It can be seen that the electrodes can be arranged in succession in differing orientation of the strip-shaped conductors in order to increase the effectiveness of the ion gate.

View e) shows the three aforementioned electrodes 60, 61, 62 next to one another. It can be seen that the electrodes 60, 61, 62 can also comprise strip-shaped conductors arranged offset to one another, as illustrated by the axis of symmetry depicted with a dotted line.

The views displayed in FIG. 13 show the electrodes in the viewing direction A of FIG. 11.

FIG. 14 shows a constructive embodiment of the ion mobility spectrometer 2 having the elements already explained above. As can be seen, a larger number of electrodes 50, 70 are present in the embodiment depicted than in the prior schematic representations.

FIG. 15 shows by way of example a spectrogram 10 recorded using the gas analyzing device comprising an ion mobility spectrometer 2 according to any of the prior figures. What is depicted is the measured ion current I in nanoamperes over time t, i.e., the drift time in milliseconds. Three measurement curves 21, 22, 23 which differ with respect to the current amplitude were recorded. The three different measurement curves were recorded at different voltages of the voltage source 71, i.e., different field strengths in the drift chamber 7. The peak values occurring in this connection are characteristic for particular substances present in the sample gas. Peak 24 is caused by the reactant ions.

To carry out a gas analysis, the described gas analyzing device 1 can be operated as follows.

The sample gas is introduced into the reaction chamber 5 in front of the ion gate 6 through the analyte inlet connector 55. At this time, the sample gas still contains electrically neutral analytes, i.e., it does not contain any analyte ions. By means of the ionization source region 4 upstream of the reaction chamber 5, an ionization can be carried out. Reactant ions in the form of $H_3O^+$ are first produced therein by the ionization source 40, 41, 42, 43 and, possibly, directly running chemical gas phase reactions between nitrogen, oxygen and water. In this connection, there are conditions in the reaction chamber, including a defined negative pressure and a defined field strength, which energetically suppress a formation of undesired water clusters and thus provide a large amount of free $H_3O^+$ reactant ions. At the same time, the drift gas is introduced into the drift chamber 7 via the drift gas supply connector 74. The drift gas flows through the drift chamber 7, the adjacent ion gate 6 and also the reaction chamber 5 adjacent thereto in order to be sucked in at the end of the enclosure body 3 by the negative-pressure generation device 11. The drift gas flowing through the reaction chamber 5 drags the introduced sample gas through the reaction chamber opposite to the drift direction predetermined by the electric field. On their way through the reaction chamber, the analyte molecules of the sample gas are ionized by charge transfer upon collision with reactant ions. The analyte ions formed in this manner then move, after ionization has taken place, opposite to their previous drift direction in the direction of the ion gate 6.

By means of the mass flow regulator 12 or else by a fixed connection, water vapor or other gases can be added to the reaction chamber 5 in order to further increase or to vary the amount of possible reactant ions. Owing to the high density of free reactant ions which thus exists in the reaction chamber, various analytes can be ionized simultaneously and it is possible to counteract a masking of substances. Furthermore, the influence of the air humidity present in the sample gas can be distinctly reduced and a direct detection of substances having proton affinities below those of water clusters in the moist sample gas mixture can be made possible in the first place.

As a result of opening of the ion gate 6 at a defined time (t=0 in FIG. 15), the analyte ions reach the drift region of the drift chamber 7 and cross said chamber in order to be detected at the ion detector 8. The amplification of the signal of the ion detector 8 is, for example, achieved using an amplifier 9 having a bandwidth optimized for the particular application, for example having a bandwidth of 60 KHz. As a result, it is possible to minimize undesired noise. The ion mobility spectrum 10 measured is a time-dependent detector current of the ion detector 8, from which it is possible to calculate the ion mobility dependent on the particular substance. The recording of the ion mobility spectrum 10 can be repeated multiple times per second, for example at a repetition frequency of 500 Hz.

Exemplary operating parameters for the reaction chamber are a field strength of 45 V per mm at a pressure of 20 mbar and a length of 100 mm of the reaction chamber 5. Exemplary parameters of the drift chamber 7 are a field strength of 12 V per mm at a pressure of 20 mbar and a drift chamber length of 100 mm. The electric field can be a static electric field, or a dynamically variable electric field.

The above-described procedure, in which a protonation with $H_3O^+$ reactant ions takes place, leading to positive analyte ions, can also be achieved in another way with pole reversal of the electric fields. For instance, negative analyte ions can be generated, it being possible for a charge transfer to take place by means of $OH^-$ reactant ions for example.

Operating the gas analyzing device 1 under negative pressure makes it simple to realize the supply of the sample gas, since the sample can be sucked into the system through the analyte inlet connector 55. Furthermore, the negative pressure favors both especially rapid response times and relatively low refractory times.

The electric field strength in the region of the ion gate 6 must, for example, be selected such that a defined opening and closing of the ion gate 6 with maximum transmission of the ions from the reaction chamber 5 to the drift chamber 7 is ensured. Optimal parameters for operation depend on the particular pressure and the field strength in the drift chamber and in the reaction chamber. In this connection, the ion gate 6 can, as desired, also be operated such that the opening duration and the time of opening of the ion gate are performed according to particular patterns, yielding at the ion detector 8 a time-dependent current, from which it is possible by transformation, for example the Hadamard or Fourier transform, of the resulting signal to calculate the ion mobility. This too can improve the signal-to-noise ratio of the spectrum obtained.

The drift chamber 7 can also be operated by a different separation method, such as FAIMS for example.

By varying the field strength in the reaction chamber, it is possible to alter the density of the free $H_3O^+$ reactant ions that are available. As a result, the influence of competing ionization processes on the spectrum obtained can be altered if necessary and thus, within a few milliseconds, additional information about the proton affinity or the electron affinity of the substances present in the spectrum can be provided.

Experiments with the gas analyzing device according to the invention show that substances having low proton affinities, for example 190 ppb 1-hexanol, are detectable with the same sensitivity at different humidities of the sample gas, for example less than 1% to 80% relative air humidity. Furthermore, a substance having a distinctly higher proton affinity, for example 500 ppb 2-nonanone, was added, which likewise did not lead to any change in the signal strength of the substance having lesser proton affinity.

By varying the field strength in the reaction chamber, it can be determined whether some substances have a relatively high proton affinity, since they can already be ionized at low field strengths. Therefore, the gas analyzing device according to the invention makes it possible to obtain additional information for identifying the particular substances.

The invention claimed is:

1. A gas analyzing device, comprising:
   a) an ion mobility spectrometer;
   b) an energy supply device which acts on a reaction chamber of the ion mobility spectrometer and which is geared to manipulating the density of free reactant ions in the reaction chamber by supply of energy,
   c) wherein the energy supply device includes a first field generation device which is geared to generating an electric field in the reaction chamber;
   d) a negative-pressure generation device which is coupled to a reaction chamber which is geared to generating a negative pressure with respect to the atmospheric pressure at least in the reaction chamber,
   e) wherein the negative-pressure generation device generates a negative pressure within a range from 2 mbar to 100 mbar absolute pressure in the reaction chamber, and f) wherein the first field generation device generates in the reaction chamber a field strength of the electric field, at which, at a given negative pressure, particles in the reaction chamber are accelerated between two collisions as a result of supply of energy by the electric field because of the thereby reduced particle density such that desired free reactant ions are cleared of undesired binding partners thereof and/or bonds of the desired reactant ions with undesired binding partners are completely or partially suppressed, g) wherein free reactant ions are free of water molecules or other unwanted binding partners bound thereto.

2. The gas analyzing device as claimed in claim 1 wherein the ion mobility spectrometer comprises:
   a) an ionization source region having an ionization source,
   b) wherein the reaction chamber is coupled to the ionization source region;
   c) a drift chamber comprising a drift gas supply connector connected to a gas supply line for supplying drift gas into the drift chamber;
   d) a switchable ion gate between the reaction chamber and the drift chamber;
   e) an ion detector at an end of the drift chamber that is facing away from the ion gate; and
   f) a second field generation device which is geared to generating an electric field in the drift chamber.

3. The gas analyzing device as claimed in claim 2, wherein the ion gate comprises at least three electrodes arranged in succession in a direction from the reaction chamber to the drift chamber.

4. The gas analyzing device as claimed in claim 3, wherein a middle electrode of the at least three electrodes of the ion gate is switchable in terms of potential by means of an electric switching mechanism of the gas analyzing device.

5. The gas analyzing device as claimed in claim 1, wherein the negative-pressure generation device is geared to generating a drift gas stream against a drift direction of the ions in the drift chamber.

6. The gas analyzing device as claimed in claim 1 wherein the negative-pressure generation device comprises a suction connector connected to a suck-off connector of the gas analyzing device, wherein the suck-off connector is arranged in front of the ion gate in a drift direction of the ions.

7. The gas analyzing device as claimed in claim 1 wherein the reaction chamber is pressure-connected to the drift chamber.

8. A method for analyzing gas by means of a gas analyzing device according to an ion mobility spectrometry method, comprising:
   manipulating a density of free reactant ions in a reaction chamber of an ion mobility spectrometer by supply of energy by means of an energy supply device acting on the a reaction chamber so as to clear desired free reactant ions of undesired binding partners thereof and/or to completely or partially suppress bonds of the desired reactant ions with undesired binding partners, wherein the reaction chamber is subjected to application of a negative pressure with respect to the atmospheric pressure within a range from 2 mbar to 100 mbar absolute pressure during the operation of gas analyzing device; and
   generating in the reaction chamber with an energy supply device in the form of a first field generation device a field strength of an electric field, at which, at a given negative pressure, particles in the reaction chamber are accelerated between two collisions as a result of supply of energy by the electric field because of the thereby reduced particle density such that desired free reactant ions are cleared of the undesired binding partners thereof and/or bonds of the desired reactant ions with undesired binding partners are completely or partially suppressed, wherein free reactant ions are free of water molecules or other unwanted binding partners bound thereto.

9. The method as claimed in claim 8, wherein the electric field generated in the reaction chamber is generated in a drift chamber in a desired drift direction of ions in the drift chamber.

10. The method as claimed in claim 8, further comprising sucking a gas to be analyzed into the reaction chamber through an analyte inlet connector of the gas analyzing device by means of the negative pressure in the reaction chamber.

11. The method as claimed in claim 8 further comprising introducing a drift gas into the drift chamber and, owing to the negative pressure in the reaction chamber guiding the drift gas through the drift chamber against a drift direction of the ions.

12. The method as claimed in claim 8 wherein the supply of energy in the reaction chamber is systematically proceeded in order to obtain information about ionizability of the substances to be analyzed with reactant ions which are bound to varying extents.

* * * * *